(12) United States Patent
Kupier et al.

(10) Patent No.: US 7,169,552 B1
(45) Date of Patent: *Jan. 30, 2007

(54) DETECTION OF POLYMORPHISMS IN AFLP FRAGMENTS USING PRIMER EXTENSION TECHNIQUES

(75) Inventors: Marius Tiemen Roelof Kupier, Kessel-Lo (BE); Hanneke Witsenboer, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/958,345

(22) PCT Filed: Apr. 10, 2000

(86) PCT No.: PCT/NL00/00235

§ 371 (c)(1),
(2), (4) Date: Jan. 2, 2002

(87) PCT Pub. No.: WO00/61801

PCT Pub. Date: Oct. 19, 2000

(30) Foreign Application Priority Data

Apr. 9, 1999 (EP) .................................. 99201112

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.1; 536/24.33

(58) Field of Classification Search .................. 435/6, 435/91.2; 536/22.1, 24.33, 23.1
See application file for complete search history.

(56) References Cited

U.S. PATENT DOCUMENTS 5,679,524 A * 10/1997 Nikiforov et al. ............. 435/6
5,874,215 A * 2/1999 Kuiper et al. ................. 435/6

FOREIGN PATENT DOCUMENTS

| EP | 534858 A1 * | 3/1993 |
| WO | WO 8910414 A1 * | 11/1989 |
| WO | WO 92/10587 | 6/1992 |
| WO | WO 96/17082 | 6/1996 |
| WO | WO 96/22388 | 7/1996 |
| WO | WO 96/31622 | 10/1996 |
| WO | WO 97/27317 | 7/1997 |
| WO | WO 97/29211 | 8/1997 |
| WO | WO 98/28438 | 7/1998 |
| WO | WO 98/30721 | 7/1998 |
| WO | WO 98/44152 | 10/1998 |
| WO | WO 99/08321 | 2/1999 |
| WO | WO 00/34518 | 6/2000 |

OTHER PUBLICATIONS

Vos et al. AELP: a new technique for DNA fingerprinting. Nucleic Acids Res., vol. 23, No. 21, pp. 4407-4414, 1995.*
Pastinen et al. Minisequencing: A specific tool for DNA analysis and diagnostics on oligonucleotide arrays Genome Res., vol. 7 (6), pp. 606-614, 1997.*
Okano et al. Characteristics of selective polymerase chain reaction (PCR) using two-base anchored primers and improvement its specificity. Electrophoresis, vol. 19, pp. 3071-3078, 1998.*
Steven E. McKenzie et al., "Parallel Molecular Genetic Analysis", *European Journal of Human Genetics*, 1998, pp. 417-429, vol. 6, No. 5.
Tomi Pastinen et al., "Minisequencing: A Specific Tool for DNA Analysis and Diagnostics on Oligonucleotide Arrays", *Genome Research*, 1997, pp. 606-614, vol. 7, No. 6, Cold Spring Harbor Laboratory Press.
Pieter Vos et al., "AFLP: A New Technique for DNA Fingerprinting", *Nucleic Acids Research*, 1995, pp. 4407-4414, vol. 23, No. 21, Oxford University Press.

* cited by examiner

Primary Examiner—Suryaprabha Chunduru
(74) Attorney, Agent, or Firm—Browdy & Neimark, PLLC (57) ABSTRACT

The present invention relates to a method for determining the genotypes of polymorphic loci amplified in a mixture of restriction fragments, using an oligonucleotide sequence that is essentially complementary to part of the target restriction fragment, and located adjacent (upstream) to the polymorphism to be detected. The method involves contacting the mixture of restriction fragments with the oligonucleotide sequence under hybridization conditions, such that when the target restriction fragment is present, a hybrid is formed between the target restriction fragment and the oligonucleotide sequence. When the resulting hybrid has at least one unpaired nucleotide of the target restriction fragment and the oligonucleotide being present, and the at least one labeled nucleotide or nucleotide analog is complementary to the at least one unpaired nucleotide of the target restriction fragment directly adjacent to the 3' end of the oligonucleotide sequence, the nucleotide sequence is extended with a labeled nucleotide or nucleotide analog, which can be detected.

14 Claims, 2 Drawing Sheets

SEQUENCE LISTING

<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gactgcgtac caattcaa                                                 18

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
gactgcgtac caattccg                                                 18

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
gactgcgtac caattccac                                                19

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gactgcgtac caattccag                                                19

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
gactgcgtac caattccat                                                19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gactgcgtac caattccca                                                19

<210> SEQ ID NO 7
<211> LENGTH: 19

```
<212> TYPE: DNA
<213> ORGANISM: Artificial Sequence
<220> FEATURE:
<223> OTHER INFORMATION: primer

<400> SEQUENCE: 7
gatgagtcct gagtaacta                                               19

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
gatgagtcct gagtaactt                                               19

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
gatgagtcct gaccgaaaa                                               19

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
gatgagtcct gaccgaaag                                               19

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
gatgagtcct gaccgaaca                                               19

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gatgagtcct gaccgaacg                                               19

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
```

-continued gatgagtcct gaccgaaga                    19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
gatgagtcct gaccgaagc                    19

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gatgagtcct gaccgaagg                    19

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gatgagtcct gaccgaata                    19

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
gatgagtcct gaccgaatt                    19

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
ggaatggagt ggattccaat                   20

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
ggaatggaga ggattccaat                   20

DETECTION OF POLYMORPHISMS IN AFLP FRAGMENTS USING PRIMER EXTENSION TECHNIQUES

REFERENCE TO RELATED APPLICATIONS

The present application is the national stage under 35 U.S.C. 371 of international application PCT/NL00/00235, filed Apr. 10, 2000 which designated the United States, and which international application was published under PCT Article 21(2) in the English language.

The present invention relates to a method for analysing nucleic acid sequences and to an array for use in such a method.

In particular, the invention relates to a method and array for determining the presence or absence of single nucleotide polymorphisms (SNP) in genomic DNA or a sample of restriction fragments derived from genomic DNA, such as AFLP fragments.

A number of methods for analyzing nucleic acid sequences are known. In general, these methods comprise immobilization of the sequences to be analysed, for instance by blotting; hybridization of the sequences with a labeled DNA- or RNA-probe; stringency washes to remove non-hybridized material; followed by detection of those sequences that have hybridized with the probe.

Such techniques are sometimes carried out after prior amplification such as by PCR- of the starting nucleic acid sequences, usually a mixture of restriction fragments from a genomic DNA. The resulting mixture of amplified fragments is then separated, for instance on the basis of differences in length or molecular weight, such as by gel-electrophoresis, and then visualised, i.e. by blotting followed by hybridization. The resulting pattern of bands is referred to as a DNA fingerprint.

Usually in DNA fingerprinting, fingerprints of closely related species, subspecies, varieties, cultivars, races or individuals are compared. Such related fingerprints can be identical or very similar, i.e. contain a large number of corresponding and therefore less informative-bands.

Differences between two related fingerprints are referred to as "DNA polymorphisms". These are DNA fragments (i.e. bands) which are unique in or for a specific fingerprint. The presence or absence of such polymorphic bands, or the pattern thereof, can be used as a genetic marker, i.e. to identify a specific species, subspecies, variety, cultivar, race or individual, to establish the presence or absence of a specific inheritable trait, of a gene, or to determine the state of a disease.

For a further discussion and definitions of DNA-fingerprinting, DNA typing, DNA polymorphisms, genotyping, PCR and similar techniques, reference is made to the discussion of the prior art in EP-0 534 858 A1, incorporated herein by reference.

The art also describes oligonucleotide arrays for analysing nucleic acid sequences or mixtures thereof, vide for instance WO 97/27317, WO 97/22720, WO 97/43450, EP 0 799 897, EP 0 785 280, WO 97/31256, WO 97/27317 and WO 98/08083.

WO 90/09455, WO 91/02087, WO 91/13075, WO 92/15712 and EP 0 123 513 all describe techniques for detecting point mutations at a predetermined site of a DNA sequence (usually genomic DNA or full length cDNA), which are generally referred to as "minisequencing". In particular, such minisequencing techniques may be used to detect differences between otherwise related or even identical DNAs at a single, specific base position. Such differences are also referred to as "Single Nucleotide Polymorphisms" or SNPs.

Minisequencing is based upon extension of a primer that hybridizes with part of the DNA sequence such that the 3' end of the primer is immediately adjacent to the point mutation. The hybrid thus obtained is contacted—usually in a single "one-tube" reaction step—with a mixture containing at least one detectable nucleotide, under conditions that extension of the primer with the detectable nucleotide takes place when the detectable nucleotide is complementary to the nucleotide present at the site of the point mutation, but no extension takes place when the detectable nucleotide does not correspond to the nucleotide present at the point mutation, so that whether or not extension of the primer takes place provides information on the nucleotide present at the site of the point mutation. (Alternatively, 2–4 differently labeled nucleotides can be used simultaneously, the extension with a specific labeled nucleotide being indicative for the presence of a complementary nucleotide at the site of mutation).

Besides being provided with a detectable functionality, the detectable nucleotide(s) and reaction mixtures/conditions used in mini-sequencing are also chosen such that, after the labeled nucleotide has been added to the primer, no further extension of the primer takes place ("terminator mixtures"). For instance, chain-terminating dideoxyribonucleoside triphosphates (ddNTPs) or thionucleotides can be used.

The method described herein differs from minisequencing at least in the following, non-limiting aspects:

a) minisequencing is used to detect/determine point mutations (SNP) at a specific, known site in the genome, which is commonly amplified by PCR using a pair of flanking primers, and is not used to determine the SNP alleles present in (a mixture) of AFLP fragments.

b) partly as a consequence of a), in minisequencing, (amplified) total genomic or cDNA is used as the starting material, not a mixture of (amplified) restriction fragments;

c) in minisequencing, usually only one or at most a small number of mutations are investigated simultaneously; in the invention, a mixture of (amplified) restriction fragments will usually be tested for the presence of at least 100 to more 1000 markers simultaneously;

d) in minisequencing, it is generally difficult to generate template DNA in multiplex form;

e) partly as a consequence of c) and d), in minisequencing, arrays containing a large number of different primers will not be used.

Selective restriction fragment amplification or AFLP, a DNA-fingerprinting technique which requires no prior knowledge of the sequence to be analysed, is described in the European patent application 0 534 858 by applicant, incorporated herein by reference. This technique generally comprises the steps of:

(a) digesting a nucleic acid, in particular a DNA, with one or more specific restriction endonucleases, to fragment said DNA into a corresponding series of restriction fragments;

(b) ligating the restriction fragments thus obtained with at least one double-stranded synthetic oligonucleotide adapter, one end of which is compatible with one or both of the ends of the restriction fragments, to thereby produce tagged restriction fragments of the starting DNA;

(c) contacting said tagged restriction fragments under hybridizing conditions with at least one oligonucleotide primer;

(d) amplifying said tagged restriction fragment hybridized with said primers by PCR or a similar technique so as to cause further elongation of the hybridized primers along the restriction fragments of the starting DNA to which said primers hybridized; and (e) identifying or recovering the amplified or elongated DNA fragment thus obtained.

The thus amplified DNA-fragments can then be analysed and/or visualised, for instance by means of gel-electrophoresis, to provide a genetic fingerprint showing bands corresponding to those restriction fragments that have been linked to the adapter, recognized by the primer, and therefore amplified during the amplification step; the resulting bands providing information on the specific restriction site pattern of the starting DNA.

For a further description of AFLP, its advantages, its embodiments, as well as the techniques, enzymes, adapters, primers and further compounds and tools used therein, reference is made to EP-A-0 534 858 and co-pending European applications 98.202.5496 and 98.202.4515, all by applicant and incorporated herein by reference. Also, in the description hereinbelow, the definitions given in paragraph 5.1 of EP-0 534 858 will be used, unless indicated otherwise.

By comparing AFLP-fingerprints from related individuals, bands which are unique for each fingerprint can be identified. These polymorfisms, referred to as "AFLP-markers", can again be used to identify a specific individual, cultivar, race, variety, subspecies or species, and/or to establish the presence or absence of a specific inherited trait, gene or disease state. The detection of such markers, however, is not the object of the present application.

Besides such "marker fragments", an AFLP-fingerprint generally also contains a number of bands which are the same for the fingerprints compared (i.e. which are not polymorphic). Such "constant" AFLP-fragments therefore cannot be used as a marker, e.g. based upon mobility differences upon gel-electrophoresis.

Nevertheless, such constant AFLP fragments may contain internal sequence variations, such as SNP, which can be detected by minisequencing. Particularly SNP located in constant AFLP fragments are of interest in this respect because both SNP alleles can be detected. In a similar fashion but dependent on the sequence context, it may be possible to detect insertion-deletion type polymorphisms located in constant AFLP fragments by minisequencing, although these can usually be detected by gel-electrophoresis as well.

Thus, generally, the present invention is directed to a method for detecting such SNP contained in these corresponding (constant) AFLP bands, which therefore can make these non-polymorphic bands, which ordinarily do not provide any useful information when conventional AFLP-fingerprinting is used, informative as genetic markers as well.

In particular, the invention aims to provide such a method for the detection of SNPs which benefits from the general advantages of AFLP-techniques, and in particular from the advantage that by using AFLP-methodology restriction fragments can be efficiently generated and provided for detection/analysis in multiplex form.

However, despite the advantages offered by AFLP-methodology, the AFLP-techniques described above still suffer from the disadvantage that the amplified fragments have to be separated (i.e. by gel-electrophoresis) and visualized (i.e. by generation of a fingerprint). These are very elaborate and time consuming procedures, which require special apparatus, such as electrophoresis and auto-radiography equipment and are limited by the resolving power of the gel system used. As a consequence, such detection by polyacrylamide gelelectrophoresis may be a limiting factor of the enormous multiplex capacity of the AFLP-technology for high throughput marker detection. The invention aims to overcome these limitations.

Thus, one of the main objects of the invention is to provide a technique for analysing nucleic acid sequences, in particular for detecting nucleic acids sequence variations such as SNP, by which a high(er) throughput compared to conventional minisequencing can be achieved, and which in particular no longer requires the use of gel-electrophoresis and preferably also avoids the use of autoradiography and/or radioactive materials, and thereby improves throughput.

This is achieved by the method of the invention, which is based upon specific extension/elongation of a oligonucleotide sequence (i.e. primer) that is complementary to (part of) the fragment to be detected, and located immediately 5' upstream of the SNP contained in this fragment, such that extension of the complementary oligonucleotide at the 3' end will only take place with the labeled ddNTP complementary to the SNP allele contained in the fragment, and will not take place with any other labeled ddNTP. Thus, the extension product(s) of the minisequencing reaction will be indicative for the SNP genotype at this locus.

This extension-based detection can be used instead of gel-electrophoresis/autoradiography, for instance in analysing AFLP reaction mixtures, in particular for routine high-throughput genotyping. For this purpose, the invention inter alia also provides an array of oligonucleotides that can be used to test an AFLP reaction mixture for the presence of several (single nucleotide) polymorphisms simultaneously, i.e. in a single detection step.

Thus, for the purposes of the detection of such "internal SNPs" as described above, the invention generally provides the main strengths of AFLP-technology—in that it allows fragments to be generated/provided for detection in multiplex form—without the limitations on throughput associated with conventional gelelectrophoresis/autoradiography and without the limitations posed by commonly used methods for amplification of templates for minisequencing based on amplification of genomic DNA or cDNA.

The invention therefore relates to a method for determining the genotypes of polymorphic loci amplified in a mixture of restriction fragments, particularly constant AFLP fragments, using an oligonucleoide sequence that is essentially complementary to part of the target restriction fragment, and located adjacent (upstream) to the polymorphism to be detected, said method comprising the steps of:

a) contacting the mixture of restriction fragments with the oligonucleotide sequence under hybridization conditions, such that when the target restriction fragment is present, a hybrid is formed between the target restriction fragment and the oligonucleotide sequence, such that resulting hybrid has at least one unpaired nucleotide of the target restriction fragment directly adjacent to the 3' end of the oligonucleotide sequence;

b) adding at least one labeled nucleotide or nucleotide analog to the mixture resulting from step a), under conditions suitable for extension of an oligonucleotide; such that when a hybrid of the target restriction fragment and the oligonucleotide is present, and said at least one labeled nucleotide or nucleotide analog is complementary to the at least one unpaired nucleotide of said target restriction fragment directly adjacent to the 3' end of the oligonucleotide sequence, the nucleotide sequence is extended with the labeled nucleotide or nucleotide analog;

c) detecting the presence or absence of any hybrid(s) with (an) added labeled nucleotide(s) or nucleotide analog(s), and/or of any oligonucleotide sequence with (an) added labeled nucleotide(s) or nucleotide analog(s).

The method of the invention may further contain one or more steps in which the hybrid formed between the target restriction fragment and the oligonucleotide sequence is separated from any restriction fragments not hybridized to a oligonucleotide sequence, as well as any other unwanted sequences or compounds. Such a step may be carried out after step a), after step b), or both.

Furthermore, it will be clear to the skilled person that the order in which the various compounds/sequences (i.e. the restriction fragments, the oligonucleotide and the labeled nucleotide) are added to/mixed with each another in steps a) and b) may be varied, and such variations will fall within the scope of the invention and claims. However, the order described above represents the most convenient way of carrying out the invention.

The invention further relates to a method for determining the SNP genotype present in one or more target restriction fragments in a mixture of restriction fragments comprising the steps of:

a) contacting the mixture of restriction fragments under hybridizing conditions with at least one oligonucleotide sequence, said oligonucleotide sequence being complementary to part of a target restriction fragment, but not to any other restriction fragment in the mixture, such that the resulting hybrid has at least one unpaired nucleotide of said target restriction fragment directly adjacent to the 3' end of the oligonucleotide sequence;

b) extending the oligonucleotide sequence with at least one labeled nucleotide or nucleotide analog, said at least one labeled nucleotide or nucleotide analog being complementary to the at least one unpaired nucleotide of said target restriction fragment directly adjacent to the 3' end of the oligonucleotide sequence;

c) detecting the oligonucleotide sequence with the added labeled nucleotide(s) or nucleotide analog(s).

Again this method can contain one or two optional steps for separating the target restriction fragments hybridized with the oligonucleotide sequence from any restriction fragments not hybridized to a oligonucleotide sequence; as well as other unwanted sequences and excess reagents.

In the method of the invention, during step a), the mixture of restriction fragments will usually be contacted simultaneously with at least 3, preferably at least 10, more preferably at least 50, most preferably at least 100 different oligonucleotide sequences, wherein each oligonucleotide sequence is most preferably specific for only one target restriction fragment, i.e. a restriction fragment harboring (or at least suspected to harbour) a (single nucleotide) polymorphism. For this purpose, in the method of the invention, the oligonucleotide sequence(s) used preferably are bound to a solid support, more preferably so as to form an array, and such arrays form a further aspect of the invention.

By "an oligonucleotide specific for a target restriction fragment" is meant that the oligonucleotide sequence is essentially complementary only to the intended target restriction fragment, but most preferably not essentially complementary to any other restriction fragment in the mixture. An oligonucleotide sequence is considered "essentially complementary to" a target restriction fragment when it has a high degree of sequence homology with the corresponding part of the target restriction fragment (determined on the basis of the full length of the oligonucleotide sequence), i.e. of at least 90%, preferably at least 95%, most preferably at least 99%.

In the present description, the restriction fragment containing the polymorphism to be detected is referred to as the "Target Sequence".

Generally, a Target Sequence will be characterized in that it is obtainable/obtained by cutting a starting DNA, usually a genomic DNA or cDNA, with at least one, but commonly with two restriction enzymes, of which preferably at least one is a "frequent cutter" restriction enzyme and at least one is a "rare cutter" restriction enzyme. (In case of genomic DNA, the "frequent cutter" serves the purpose of reducing the size of the restriction fragments to a range of sizes which are amplified efficiently and in a manner compatible with the detection technique used, and the "rare cutter" serves the purpose of controlling the total number of fragments generated. For both, reference is made to EP-A-0 534 858 and EP-A-0 721 987 by applicant, incorporated herein by reference.) Non-limiting examples of suitable frequent cutter enzymes include MseI and TaqI. Non-limiting examples of commercially available rare cutters include PstI, HpaII, MspI, ClaI, HhaI, EcoRI, EcoRII, BstBI, HinP1, HinDIII, MaeII, BbvI, PvuII, XmaI, SmaI, NciI, AvaI, HaeII, SalI, XhoI, BstYI, BamHI, BglII and PvuII, of which PstI, HpaII, MspI, ClaI, EcoRI, EcoRII, BstBI, HinP1, HinDIII, BamHI, BglII and MaeII are preferred.

Preferably, the Target Sequence is a restriction fragment as present in a mixture of restriction fragments, more preferably an amplified restriction fragment as present in a mixture of restriction fragments and/or amplified restriction fragments.

Even more preferably, the Target Sequence is a restriction fragment that corresponds to a "constant" AFLP-fragment (or part thereof), e.g. a restriction fragment amplified by AFLP as present in reaction mixture obtained after AFLP amplification.

The oligonucleotide sequence used to detect the Target Sequence will be referred to hereinbelow as the "Detection Oligonucleotide", the "Detection Sequence" or the "Detection Primer", which terms are to be considered equivalent.

Each Detection Sequence should at least in part be complementary to a specific Target Sequence, as defined above. The Detection Sequence may be any nucleic acid (i.e. DNA or RNA) but is preferably DNA. The Detection Sequence will generally have a size of about 10 to 100 base pairs, preferably about 20 to 50 base pairs. The Detection Sequences may all be of the same size, or may be of different sizes. Also, when immobilized on an array as described below, the Detection Sequences may further contain a "tail"—such as a polyT sequence—for and improved accesibility to the Target Sequence.

The Detection Sequence can be obtained in any suitable manner. For instance, when one or more constant AFLP-fragments harboring one or more single nucleotide polymorphisms have been identified in an AFLP fingerprint of a specific set of (preferably related) individuals, the sequence of each band/fragment may be determined in a manner known per se, and Detection Sequences may be synthesized that are complementary to any part of the sequence of each of the constant bands, i.e. using an automated DNA-synthesizer or in any other manner known per se. Also, solid phase nucleic acid synthesis techniques may be used, which may result directly in an array with the desired Detection Sequences, as described below. Furthermore, the Detection Sequence may be obtained using known techniques of genetic engineering, for instance by primer extension using the Target Sequence as a template, and/or by using one or more restriction enzymes, optionally using amplification.

Also, the Detection Sequence may obtain one or more "alternative nucleosides" as described in applicants copending European application 98202451.1, so that the Detection Sequence is an "alternative primer" as described therein. Similarly, in step b), the Detection Sequence may be extended with such an alternative nucleoside/nucleotide, provided with a label. Examples thereof include the bases Inosine (I) and Uracil (U), as well as dUTP and dITP, and these are included within the term "labeled nucleotide analog" as mentioned above. It is to be understood that the presence of such alternative nucleosides does not prevent the Detection Sequence and the Target Sequence to be essentially complementary to one another as defined above.

As mentioned above, the Detection Sequences are preferably bound to a solid support, more preferably so as to form an array. Such an array will generally comprise at least 10, more specifically at least 100, more preferably at least 1000 different Detection Sequences. For a "high-density array" or "micro-array", the total number of Detection Sequences can be in the range of 1000–100.000 per $cm^2$ of surface area.

The Detection Sequences will generally be bound to the carrier in such a way that each Detection Sequence is attached to, and corresponds with, a specific, distinct part of the carrier, so as to form an independently detectable area on the carrier, such as a spot or band. This makes it possible to "read" the array by scanning (i.e. visually or otherwise) the areas to which each Detection Sequence (i.e. a sequence corresponding to a marker of interest) is attached. For a general description of such arrays, reference is made to applicants co-pending PCT application "Method for the analysis of AFLP reaction mixtures using primer extension techniques" filed Apr. 10, 2000.

In step a) of the invention, the one or more Detection Sequences (or the array of the Detection Sequences) are contacted with the sample (i.e. mixture of restriction fragments) to be analysed under hybridizing conditions known per se. Suitable hybridisation conditions (i.e. buffers used, salt strength, temperature, duration) can be selected by the skilled person, on the basis of experience or optionally after some preliminary experiments. These conditions may vary, depending on factors such the size of the Detection Sequences, the CG-content of the Detection Sequences and whether the Detection Sequence or Target Sequence is bound to an array as described below.

Suitable hybridisation conditions are for instance described in Sambrook et al., *Molecular Cloning: A Laboratory manual*, (1989) 2nd. Ed. Cold Spring Harbour, N.Y.; Berger and Kimmel, "Guide to Molecular Cloning Techniques", *Methods in Enzymology*", (1987), Volume 152, Academic Press Inc., San Diego, Calif.; Young and Davis (1983) *Proc. Natl. Acad. Sci.(USA)* 80: 1194; *Laboratory Techniques in Biochemistry and Molecular Biology, Vol. 24, Hybridization with Nucleic Acid Probes*, P. Thijssen, ed., Elsevier, N.Y. (1993), as well as WO 97/43450. EP-A-0 799 897, WO 97/27317, WO 92/10092, WO 95/1195, WO 97/22720 and U.S. Pat. No. 5,424,186, all incorporated herein by reference, and generally may comprise temperatures between 25–70° C., preferably 35–65° C., a duration of between 1 minute and 30 hours, preferably about 15 minutes to 2 hours, and the use a suitable buffer, such as a Tris-buffer.

The hybridisation conditions are preferably chosen such that each Detection Sequence will only form a hybrid (duplex) with a Target Sequence with which the Detection Sequence is essentially complementary as defined above, and otherwise will not form any hybrid.

Especially preferred hybridisation conditions are those known per se for primer extension, such as the primer extension conditions used in minisequencing techniques, i.e. as described in WO 90/09455, WO 91/02087, WO 91/13075, WO 92/15712 and EP 0 123 513. This has the advantage that both step a) and step b) above can be carried out under the same "primer extension conditions", i.e. in a single reaction, using the same buffer, etc, optionally under repeated temperature cycling.

When the mixture of restriction fragments is contacted with a Detection Sequence, and a Target Sequence for said Detection Sequence is present, a hybrid between the Target Sequence and the Detection Sequence will be formed. Said hybrid should be such—i.e. the Detection Sequence should be designed to be complementary to the Target Sequence such—that there is at least one unpaired nucleotide of the Target Sequence directly adjacent to the 3' end of the Detection Sequence, such that, in step b), the Detection Sequence is extended, e.g. with preferably with at most five, preferably at least most three, and most preferably only one nucleotide.

During step b) of the method of the invention, the at least one position corresponding to said unpaired nucleotide(s) in the Target Sequence is "filled in" with at least one nucleotide, by means of elongation of the Detection Sequence, in which the Target Sequence serves as a template for an extension reaction. Therefore, if the Target Sequence that corresponds to the specific Detection Sequence is not present, no hybrid will be formed, and said Detection Sequence will not be extended, showing that the (allelic variant of the) Target Sequence was not present in the starting mixture.

Preferably, said nucleotides used in step b) to extend the Detection Sequence nucleotides or nucleotide analogs that can be detected in a manner known per se, for instance by means of a detectable label, and such a nucleotide is referred to as a "Detectable Nucleotide". For a further description of such "Detectable Nucleotides", reference is again made to applicants co-pending PCT application "Method for the analysis of AFLP reaction mixtures using primer extension techniques" filed Apr. 10, 2000.

According to one embodiment of the invention, the mixture used in step b) for extending the Detection Sequence contains only one (type of) Detectable Nucleotide, i.e. one or more Detectable Nucleotides that are complementary to only one of A, T, C or G. Under these conditions, only those target sequences that: 1) can hybridize succesfully with the Detection Sequence; and 2) have in their sequence, on a position directly adjacent to the part of the sequence that hybridizes with the Detection Sequence, a nucleotide complementary to the Detectable Nucleotide, will lead to extension of the Detection Sequence with the Detectable Nucleotide and thereby to a positive signal, indicative for the presence of the corresponding allelic variant said Target Sequence in the mixture to be analysed.

In another embodiment, the mixture used in step b) for extending the Detection Sequence will contain two, three or four different Detectable Nucleotides. By "different Detectable Nucleotide" is meant that each Detectable Nucleotide is complementary to a different unpaired nucleotide A, T, G or C on the Target Sequence, and each Detectable Nucleotide is labeled in such a way that it can be distinguished—i.e. using a suitable detection technique—from the other Detectable Nucleotide(s) present in the extension reaction and/or the extended Detection Sequence, so that extension of the Detection Sequence with a specific Detectable Nucleotide can be indicative for the presence of a specific nucleotide on the corresponding position of the Target Sequence.

The conditions for extension of the Detection Sequence with the Detectable Nucleotide may include all conditions known per se for the extension of a oligonucleotide or primer hybridized to a nucleic acid template, for instance as described in the art for minisequencing, such as in WO 90/09455, WO 91/02087, WO 91/13075, WO 92/15712 and/or EP 0 123 513. These include use of a polymerase such as E. coli DNA polymerase, Klenow fragment, bacteriophage T7 DNA polymerase, bacteriophage T4 DNA polymerase, Taq DNA polymerase and AMV transcriptase, in a suitable buffer, such as an aqueous buffer containing Mg-salts, at a temperature of 20–80° C., preferably 30–70° C.

Optionally, after the hybridization of step a), and/or after the extension reaction of step b), any restriction fragments not hybridized to a Detection Sequence, as well as any other unwanted sequences, compounds, or excess reagents, may be removed, for instance by washing the array.

After the Detection Sequence in the Target Sequence/Detection Sequence duplexes have been extended with the Detectable Nucleotide ("DN"), the resulting mixture is analysed to determine which Detection Sequence have been extended with a DN, using a suitable detection technique. This analysis may be carried out while the Detection Sequence(s) are still hybridized to the corresponding Target Sequence(s), or Target Sequence(s) may be removed/separated from the Detection Sequence(s) in a separate step prior to dectection and analysis.

For a more general description of techniques/methodology involving the use of Target Sequences, Detection Sequences, Detectable Nucleotides, arrays, etc. as used hereinabove for the purposes of the present invention, reference is again made to applicants co-pending PCT application "Method for the analysis of AFLP reaction mixtures using primer extension techniques" filed Apr. 10, 2000, and in particular to FIG. 9 thereof.

The analysis of the array may be carried out in any manner known per se, including optical techniques, spectroscopy, chemical techniques, biochemical techniques, photochemical techniques, electrical techniques, light scattering techniques, colorimetric techniques, radiography techniques, etc., depending on the label in the Detectable Nucleotides. Suitable techniques are for instance described in WO 97/27317, WO 97/22720, WO 97/43450, EP 0 799 897, WO 97/31256, WO 97/27317 and WO 98/08083. For instance, the array may be inspected visually or by (confocal) microscopy; by spectroscopy; using photographic film, electronic detectors or a CCD camera; by colorimetric or (bio)chemical assay; or by any other suitable method, for which again reference is made to WO 97/27317, WO 97/22720, WO 97/43450, EP 0 799 897, WO 97/31256, WO 97/27317 and WO 98/08083. Automated scanning equipment based upon such techniques may also be used.

Generally, the signal detected will be indicative for the (Detectable) Nucleotide with which the Detection Sequence has been extended, which in turn will be indicative for the base(s) present in the Target Sequence—e.g in the hybrid of the Target Sequence and the Detection Sequence—directly adjacent the 3'-end of the Detection Sequence. Thus, in this manner, the method of the invention not only allows for the detection of (any) SNPs in the Target Sequence—e.g. directly adjacent to the Detection Sequence—but makes it possible to determine which specific base is present at the locus of the SNP in the Target Sequence.

Optionally, the relative intensity or absolute magnitude of a signal generated by a Detectable Nucleotide on a specific site on the array may be used as a relative indication or an absolute measure of the amount of the corresponding allelic variant of the Target Sequence fragment present in the original sample, for instance as described in WO 98/08083.

The array of the invention can conveniently be provided as a kit of parts comprising the array and other components for use with the array, such as hybridization buffers, extension buffers, polymerase, labeled nucleotides, containers/packaging and manuals, as well as components for AFLP-kits known per se. The array of the invention may even be in the form of a hand-held device such as a dipstick.

In principle, method and arrays of the invention can be applied to, and can be used for, any purpose for which an SNP can be used and/or identified. This includes, but is not limited to, all the uses described in the art for SNPs known per se, such as detection of (SNP-)alleles.

In a further aspect, the invention relates to results and/or data obtainable by analysing a mixture of restriction fragments with the method of the invention. These results or data may for instance be in the form of an image, of a score, of digital or analog data, or in another suitable form, and may optionally be stored on a suitable data carrier, including paper, photographic film, computer disc of files, a database, etc. This data may be as directly obtained from analysing or scoring the array, or may have been processed further.

The invention will now be further illustrated by means of the following non-limiting Experimental Part, as well as by the enclosed Figures, which show.

EXPERIMENTAL PART

Example 1

The overall objective of the invention is to develop a high throughput DNA marker system for gene mapping and genetic diagnostics, and to demonstrate its utility for genetic analysis of human populations as a prelude to the mapping of complex diseases.

For future molecular diagnostic purposes the aim will be to generate many datapoints at low cost. This will only be possible by using procedures that do not need the costly and time consuming step of slabgel electrophoresis. The strategy to use series of mutation-dedicated oligonucleotides bound to a solid support should allow the simultaneous detection of hundreds to thousands of point mutations, thereby generating a comprehensive genetic fingerprint of an individual. Current estimates of the cost of such mass-produced chips are in the tens of dollars, a moderate price for routine diagnostic purposes in humans. Although the detection of many point mutations on a chip format is feasible on relatively small numbers (<200) of SNPs, for higher numbers of markers there are a number of problems to be solved:

1. It is currently unclear as to how the target molecules for chip-analysis should be amplified, in an efficient way.

2. Having oligos on a chip for hybridization to a complex mixture of target sequences poses problems in sequence-specific hybridization. This can only be remedied by using several oligos to verify each possible polymorphic site. This limits the capacity of the system. In addition, sequence-dependent hybridization efficiencies make it necessary to be able to detect hybridization over a wide dynamic range.

In this Example, we aim to design a better alternative for detection of SNPs on a microchip format. AFLP allows the selective amplification of large sets of restriction fragments. The AFLP technology to date is the most efficient multiplex PCR technique available, in effect capable of quantitative whole-genome amplification. Therefore, the AFLP technique is the perfect enabling technology to prepare any number of templates for SNP analysis. To alleviate the problems with low specificity of the hybridization assay, the single nucleotide primer extension reaction used in the minisequencing assay offers a superior technology due to the inherent specificity of DNA polymerases.

A. Material and Methods

Human population DNA samples; of each population 10 male and 10 female samples were present.

Bosnian (muslims, Tuzla)

Saami (Lovozero, Russia)

Hanti (Ob-river, Siberia)

Mansi (Ob-river, Siberia)

Somali (Somalia, Africa)

B. Oligo Synthesis

Oligonucleotides were synthesized according to standard procedures, or purchased from MWG—Biotech GmbH (Germany).

C. AFLP Analysis on Human DNA

AFLP templates were prepared according to standard procedures (Vos et al. 1995), using EcoRI and TaqI as the enzyme combination. AFLP reactions were preceeded by preamplifications with one selective nucleoside on each primer. AFLP reactions were performed with primer combinations with 3 selective nucleosides on each primer.

For amplifying the fragments harbouring the Y-chromosomal SNPs an adaptation of the AFLP protocol was used that uses only one restriction enzyme (MseI) for template preparation.

```
AFLP primer sequences (5'-3'):
E11    GACTGCGTACCAATTC AA       (SEQ ID NO:1)

E17    GACTGCGTACCAATTC CG       (SEQ ID NO:2)

E48    GACTGCGTACCAATTC CAC      (SEQ ID NO:3)

E49    GACTGCGTACCAATTC CAG      (SEQ ID NO:4)

E50    GACTGCGTACCAATTC CAT      (SEQ ID NO:5)

E51    GACTGCGTACCAATTC CCA      (SEQ ID NO:6)

M59    GATGAGTCCTGAGTAA CTA      (SEQ ID NO:7)

M62    GATGAGTCCTGAGTAA CTT      (SEQ ID NO:8)

T31    GATGAGTCCTGACCGA AAA      (SEQ ID NO:9)

T33    GATGAGTCCTGACCGA AAG      (SEQ ID NO:10)
```

```
                  -continued
T35    GATGAGTCCTGACCGA ACA      (SEQ ID NO:11)

T37    GATGAGTCCTGACCGA ACG      (SEQ ID NO:12)

T39    GATGAGTCCTGACCGA AGA      (SEQ ID NO:13)

T40    GATGAGTCCTGACCGA AGC      (SEQ ID NO:14)

T41    GATGAGTCCTGACCGA AGG      (SEQ ID NO:15)

T43    GATGAGTCCTGACCGA ATA      (SEQ ID NO:16)

T46    GATGAGTCCTGACCGA ATT      (SEQ ID NO:17)
```

D. AFLP Analysis on Plant DNA

AFLP templates were prepared according to standard procedures (Vos et al. 1995), using EcoRI and MseI as the enzyme combination: AFLP reactions were preceeded by preamplifications with one selective nucleoside on each primer. AFLP reactions were performed with primer combinations with 2 or 3 selective nucleosides on each primer.

E. Sequence Analysis

AFLP-fragments were cut out from a dried polyacrylamide gel, reamplified with the same primer combination that was used to generate the fingerprint and either sequenced directly using AFLP primers, or cloned into plasmid pCR2.1-TOPO (TOPO TA Cloning kit, Invitrogen) and sequenced using M13 forward and reverse primers. Sequencing reactions were performed using the dye-terminator sequencing kit purchased from Perkin-Elmer and were analyzed on an ABI 377 sequencer.

Minisequencing on ss DNA was performed according to Syvänen et al. (1990, 1993) with the following modifications. AFLP reactions were performed using one biotinylated primer and one standard primer and biotinylated AFLP products were collected on streptavidine-coated magnetic beads (Dynal). Subsequently, minisequencing was performed on either 1) the biotinylated strand that remained bound to the beads after denaturation with NaOH or 2) the non-biotinylated strand that could be separated from the biotinylated strand by boiling and pipetting off the supernatant. Subsequently, further purification of the supernatant was performed by adding shrimp alkaline phosphatase and exonuclease I to get rid of any leftover primer and dNTPs (Chen et al. 1997).

The minisequencing reaction on the biotinlyated strand was carried out in 10 mM Tris-HCl pH 9.5, 50 mM KCl, 20 mM MgCl$_2$, 0.02% Tween-20, 2 µl of 5 µM detection primer, 0.3 µl labeled $^{33}$P ddNTP (Amersham) complementary to the nucleotide to be detected, 1 unit of Thermosequenase and water to a total volume of 50 µl. The reaction was incubated for 10' at 50° C., beads were washed and minisequencing products were released from the beads by denaturation in formamide dye at 94° C., spotted on Whatman paper and exposed to Fuji phosphoimage screens for 16 hours. Patterns were visualized using a Fuji BAS-2000 phosphoimage analysis system (Fuji Photo Film Company Ltd. Japan).

The minisequencing reaction on the non-biotinlyated strand was performed 1) in the same way as described above, however a biotinylated detection primer was used: ds products were collected on streptavidine-coated magnetic beads (Dynal), beads were washed, spotted on filters and exposed to Fuji phosphoimage screens for 16 hours. Patterns were visualized using a Fuji BAS-2000 phosphoimage analysis system (Fuji Photo Film Company Ltd, Japan). 2) Minisequencing reactions were performed on glass slides with primers attached to them. Slides were washed and exposed to Fuji phosphoimage screens for 16 hours. Patterns were visualized using a Fuji BAS-2000 phosphoimage analysis system (Fuji Photo Film Company Ltd, Japan).

Minisequencing on ds DNA was performed according to Syvänen et al. (1990, 1993) with the following adaptations. AFLP reactions were performed and treated with shrimp alkaline phosphatase and exonucleaseI to get rid of any leftover primer and dNTPs (Chen et al. 1997). Subsequently, minisequencing was performed in 10 mM Tris-HCl pH 9.5, 50 mM KCl, 20 mM $MgCl_2$, 0.02% Tween-20, 2 µl of 5 PM biotin labeled detection primer, 0.3 µl labeled $^{33}P$ ddNTP (Amersham) complementary to the nucleotide to be detected, 5 µl 2 µM ddNTPs, 1 unit of Thermosequenase. The PCR profile consisted of 35 cycles 15" 95° C., 30" 58° C. (Chen et al. 1997). Minisequencing products were collected on streptavidine-coated magnetic beads (Dynal), beads were washed, spotted on Whatman paper and exposed to Fuji phosphoimage screens for 16 hours. Patterns were visualized using a Fuji BAS-2000 phosphoimage analysis system (Fuji Photo Film Company Ltd, Japan).

Coating of glass slides and binding of amino primers was performed as described by Guo et al. (1994). 1 µl of primers was spotted manually.

F. Results: Use of AFLP for the Detection of Y-Polymorphisms

Human DNA samples were pooled into either male or female pools: for the screening of male-specific fragments as many different male and female samples as possible were collected in one pool. For the screening for Y-polymorphisms, 3 different male pools were made with pooled DNA's from only 1 or 2 different populations to be able to detect quantitative differences in number of alleles present in a pool.

Figure 1:
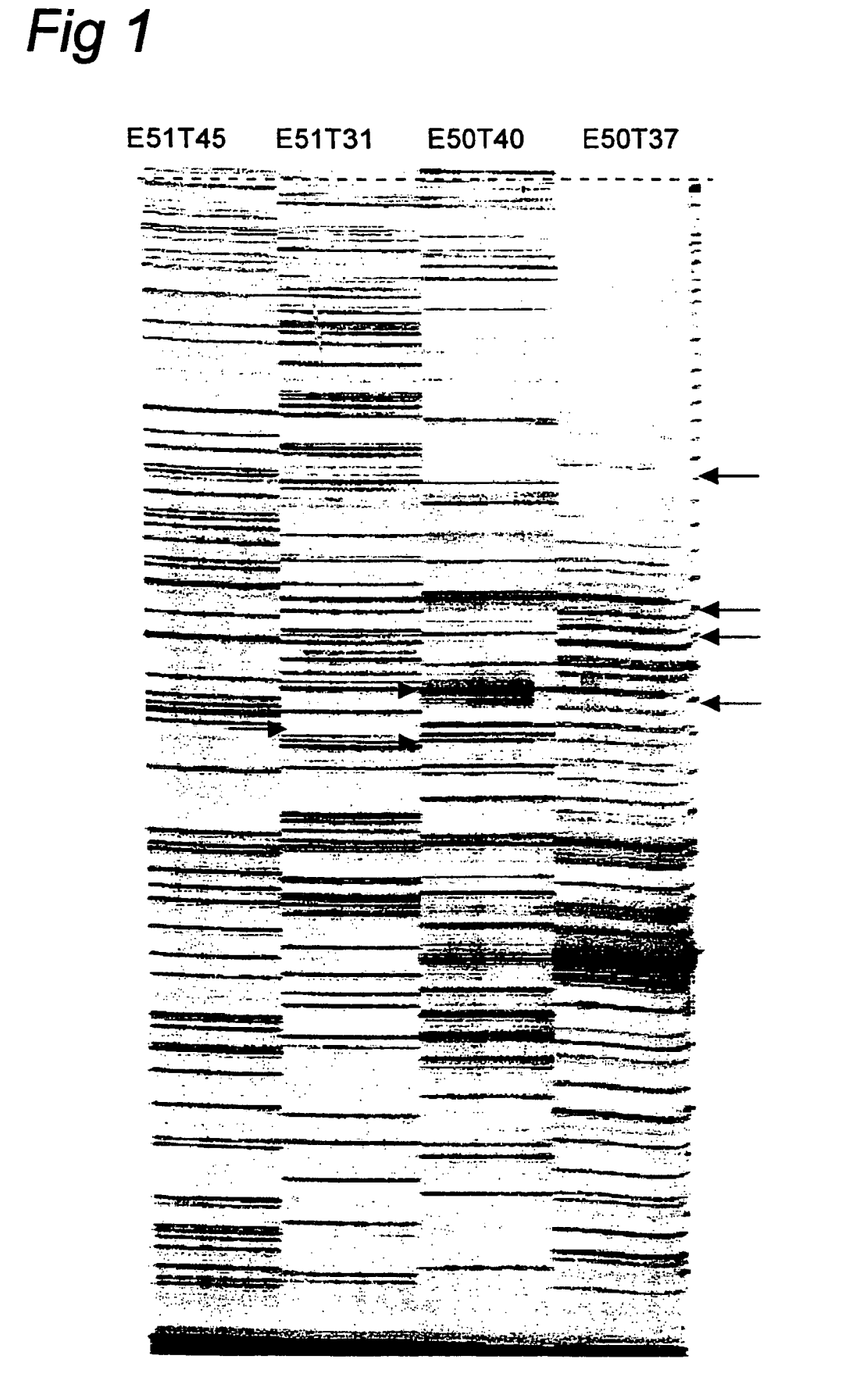
FIG. 1: Screening for Y-fragments and Y-polymorphisms using 5 male pools and one female pool, respectively. Primer combinations used to generate the fingerprints are indicated above the panels. Y-fragments are indicated with arrows.
Figure 2:
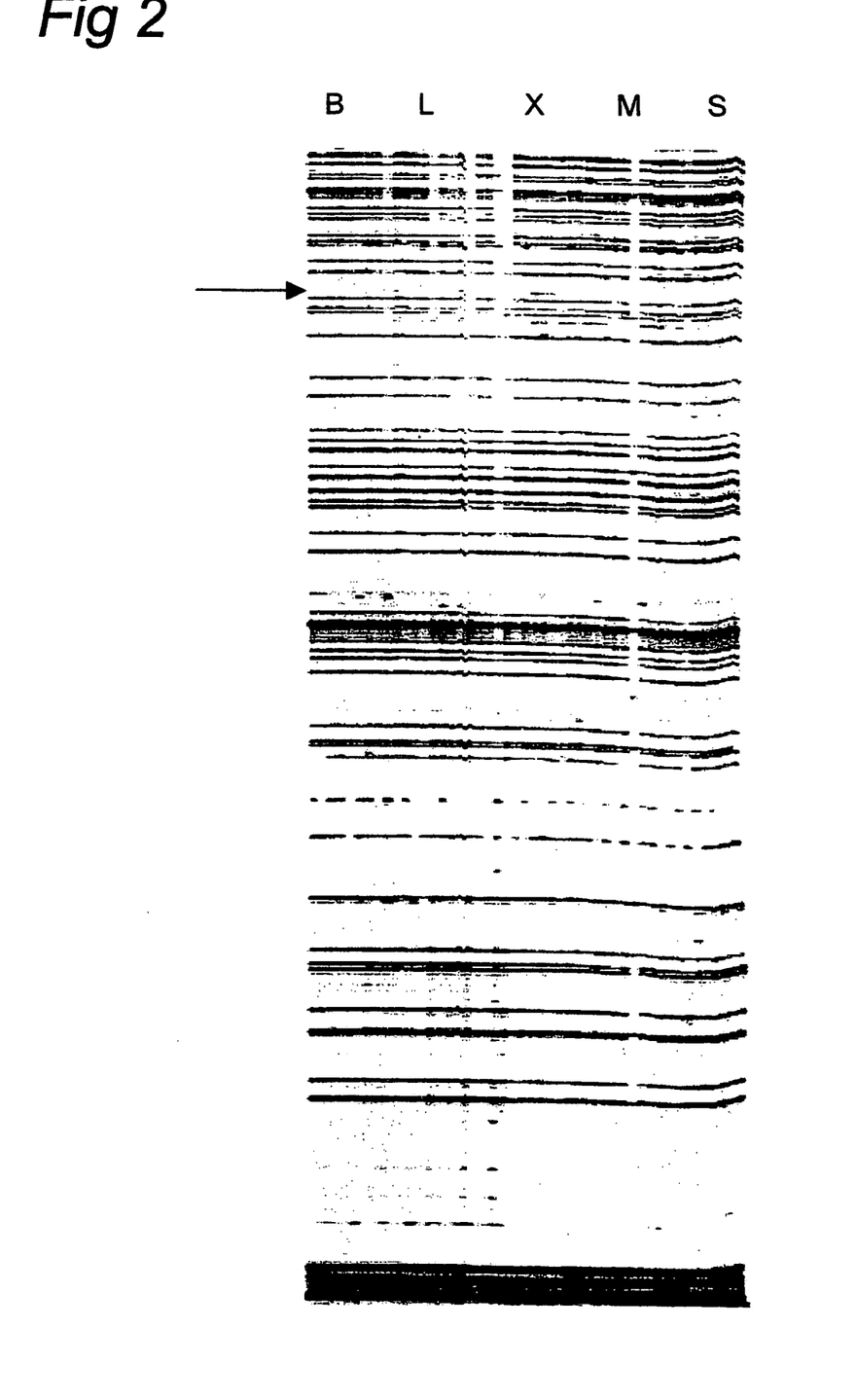
FIG. 2: Fingerprints of 48 male individuals generated with primer combination E48T46. The 330 bp Y-polymorphic fragment is indicated. Also the different populations, the individuals come from, are indicated (Bosnian: lanes B 1–12, Saami: lanes L 13–22, Hanti: lanes X 23–32, Mansi: lanes M 33–42, Somali lanes S 43–48).

96 EcoRI/TaqI primer combinations were used to screen for male specific fragments; with 12 EcoRI/TaqI primer combinations out of those, male-specific fragments were detected (table 1, FIG. 1). A number of male-specific fragments isolated from AFLP fingerprints on pools was directly sequenced to search for male-specific polymorphisms between pools and within pools: for Y-polymorphisms within pools ambiguous sequence data were expected. This approach was not successful, since it was hard to isolate Y-chromosome derived fragments not contaminated with other AFLP fragments and, therefore, ambiguous sequence information was obtained anyway. As an alternative strategy, male-specific fragments isolated from AFLP fingerprints on pools were cloned, and 18 clones per fragment were sequenced. Sequences were compared to look for SNPs. This was done for 3 male-specific fragments. Y-fragments sequenced in one or both ways are indicated (table 1). One putative SNP in a Y-fragment of 330 bp generated with primer combination E48T46 was detected this way (table 2). By fingerprinting the male and female individuals with this primer combination also an AFLP polymorphism for this fragment was detected (FIG. 2). There were no female individuals from which this fragment was amplified. The AFLP polymorphism was present within all 5 groups of male individuals, however in many cases the fragment was badly amplified and hard to score.

TABLE 1

Primer combinations detecting Y-chromosome derived AFLP fragments. The size of the Y-chromosome fragments is indicated in basepairs. Y-chromosome fragments sequenced in pools or sequenced as clones are indicated.

| Primer Combination | Y-fragments in bp | Sequenced in pools | Sequenced as clones |
| --- | --- | --- | --- |
| E17T35 | 170 | | |
| E17T43 | 170 | | |
| | 60 | | |
| | 55 | | |
| E48T31 | 285 | | X |
| | 170 | X | X |
| E48T39 | 170 | | |
| | 155 | | |
| E48T43 | 170 | X | |
| E48T46 | 330 | X | X |
| | 310 | X | |
| E49T35 | 55 | X | |
| E49T41 | 65 | | |
| E50T33 | 170 | | |
| E50T37 | 255 | | |
| | 215 | | |
| | 205 | X | |
| | 170 | X | |
| E50T40 | 170 | | |
| | 155 | | |
| E51T31 | 160 | | |

TABLE 2

The putative SNP in fragment E48T46-330 as determined by sequencing 18 random clones harbouring this fragment; the SNP is located at position 97 from the TaqI site of the AFLP fragment.

88- GGAATGGAGTGGATTCCAAT-107 (5'-3') (SEQ ID NO:18)

88- GGAATGGAGAGGATTCCAAT-107 (5'-3') (SEQ ID NO:19)

G. Conclusions

The level of polymorphism in the human Y-chromosome is extremely low. AFLP is an efficient way to screen for male-specific AFLP fragments and AFLP polymorphisms. Sequencing of male-specific AFLP fragments in pools to detect SNPs was not succesful. Sequencing of cloned male-specific AFLP fragments resulted in detection of one putative SNP, however, this approach is very inefficient.

H. Detection of AFLP Markers by Minisequencing

Minisequencing was explored as a method to detect AFLP fragments. Minisequencing using AFLP template can be applied as a non-random method for SNP detection by, using predetermined sequence information. By the method of the invention, using internal AFLP primers, minisequencing can also be applied to detect SNPs. Prerequisite is that at least 2 alleles are known, which often is not the case in AFLP, that mostly generates dominant markers.

The invention claimed is:

1. A method for detecting a single nucleotide polymorphism located within an amplified AFLP target fragment, which is not an AFLP marker fragment that serves to distinguish between AFLP fingerprints, using an oligonucleotide sequence that is specific for said AFLP target fragment, and located adjacent (upstream) to the single nucleotide polymorphism to be detected, said method comprising the steps of:
   a) generating a mixture of PCR amplified restriction fragments using the AFLP method, by:
      digesting whole genomic DNA or cDNA with one or more restriction endonucleases to generate a mixture of fragments;
      ligating the restriction fragments obtained with at least one double stranded synthetic oligonucleotide adapter to generate tagged restriction fragments; and
      amplifying said tagged restriction fragments by PCR to generate a mixture of PCR amplified restriction fragments;
   b) contacting said mixture of amplified restriction fragments with said target-fragment specific oligonucleotide sequence under hybridization conditions, using a single target-fragment specific oligonucleotide per AFLP target fragment such that when the target restriction fragment is present, a hybrid is formed between the target restriction fragment and the oligonucleotide sequence, such that the resulting hybrid has at least one unpaired nucleotide of the target restriction fragment directly adjacent to the 3' end of the oligonucleotide sequence, wherein said target-fragment specific oligonucleotide is complementary only to the intended target restriction fragment but not complementary to any other restriction fragment in the mixture;
   c) adding at least one labeled nucleotide or nucleotide analog to the mixture resulting from step b), under conditions suitable for extension of an oligonucleotide, such that when a hybrid of the target restriction fragment and the oligonucleotide is present, and said at least one labeled nucleotide or nucleotide analog is complementary to the at least one unpaired nucleotide of said target restriction fragment directly adjacent to the 3' end of the oligonucleotide sequence, the nucleotide sequence is extended with the labeled nucleotide or nucleotide analog; and
   d) detecting the presence or absence of any hybrid(s) with (an) added labeled nucleotide(s) or nucleotide analog(s), or of any oligonucleotide sequence with (an) added labeled nucleotide(s) or nucleotide analog(s).

2. The method according to claim 1, wherein during step c), the at least one labeled nucleotide or nucleotide analogue is such that the extension of the oligonucleotide sequence is terminated after the oligonucleotide sequence has been extended with the at least one labeled nucleotide or nucleotide analogue.

3. The method according to claim 2, wherein during step c), the oligonucleotide sequence is extended by a single labeled nucleotide or nucleotide analogue.

4. The method according to claim 3, wherein the oligonucleotide sequence is immobilized on a solid support.

5. The method according to claim 4, wherein the oligonucleotide sequences are immobilized on said solid support in the form of an array.

6. The method according to claim 1, wherein the mixture of restriction fragments is obtained by restricting the starting DNA with at least two restriction enzymes.

7. The method according to claim 1, wherein the mixture of restriction fragments is obtained by restricting the starting DNA with at least one rare cutter restriction enzyme and at least one frequent cutter restriction enzyme.

8. The method according to claim 1, wherein during step c), the oligonucleotide sequence is extended by a single labeled nucleotide or nucleotide analogue.

9. The method according to claim 1, wherein the oligonucleotide sequences are immobilized on a solid support.

10. The method according to claim 1, wherein the PCR in step (a) amplifies a subset of said tagged restriction fragments.

11. The method according to claim 1, wherein the same oligonucleotide extension conditions are used for the hybridization of step b) and for the oligonucleotide extension of step c).

12. The method according to claim 1, wherein step d) comprises the step of detecting the presence or absence of any hybrid(s) with (an) added labeled nucleotides or nucleotide analog(s) and of any oligonucleotide sequence with (an) added labeled nucleotide(s) or nucleotide analog(s).

13. A method for detecting a single nucleotide polymorphism located within an amplified non-AFLP marker target fragment, using an oligonucleotide sequence that is specific for said AFLP target fragment, and located adjacent (upstream) to the single nucleotide polymorphism to be detected, said method comprising the steps of:
   b) a) generating a mixture of PCR amplified restriction fragments using the AFLP method, by:
      digesting whole genomic DNA or cDNA with one or more restriction endonucleases to generate a mixture of fragments;
      ligating the restriction fragments obtained with at least one double stranded synthetic oligonucleotide adapter to generate tagged restriction fragments; and
      amplifying said tagged restriction fragments by PCR to generate a mixture of PCR amplified restriction fragments;
   b) contacting said mixture of amplified restriction fragments with said target-fragment specific oligonucleotide sequence under hybridization conditions, using a single target-fragment specific oligonucleotide per AFLP target fragment such that when the target restriction fragment is present, a hybrid is formed between the target restriction fragment and the oligonucleotide sequence, such that the resulting hybrid has at least one unpaired nucleotide of the target restriction fragment directly adjacent to the 3' end of the oligonucleotide sequence, wherein said target-fragment specific oligonucleotide is complementary only to the intended target restriction fragment but not complementary to any other restriction fragment in the mixture;
   c) adding at least one labeled nucleotide or nucleotide analog to the mixture resulting from step b), under conditions suitable for extension of an oligonucleotide, such that when a hybrid of the target restriction fragment and the oligonucleotide is present, and said at least one labeled nucleotide or nucleotide analog is complementary to the at least one unpaired nucleotide of said target restriction fragment directly adjacent to the 3' end of the oligonucleotide sequence, the nucleotide sequence is extended with the labeled nucleotide or nucleotide analog; and
   d) detecting the presence or absence of any hybrid(s) with (an) added labeled nucleotide(s) or nucleotide analog(s), or of any oligonucleotide sequence with (an) added labeled nucleotide(s) or nucleotide analog(s).

14. A method for detecting an internal single nucleotide polymorphism located within an amplified AFLP target fragment, using an oligonucleotide sequence that is specific for said AFLP target fragment, and located adjacent (upstream) to the single nucleotide polymorphism to be detected, said method comprising the steps of:

c) a) generating a mixture of PCR amplified restriction fragments using the AFLP method, by:
  digesting whole genomic DNA or cDNA with one or more restriction endonucleases to generate a mixture of fragments;
  ligating the restriction fragments obtained with at least one double stranded synthetic oligonucleotide adapter to generate tagged restriction fragments; and
  amplifying said tagged restriction fragments by PCR to generate a mixture of PCR amplified restriction fragments;
b) contacting said mixture of amplified restriction fragments with said target-fragment specific oligonucleotide sequence under hybridization conditions, using a single target-fragment specific oligonucleotide per AFLP target fragment such that when the target restriction fragment is present, a hybrid is formed between the target restriction fragment and the oligonucleotide sequence, such that the resulting hybrid has at least one unpaired nucleotide of the target restriction fragment directly adjacent to the 3' end of the oligonucleotide sequence, wherein said target-fragment specific oligonucleotide is complementary only to the intended target restriction fragment but not complementary to any other restriction fragment in the mixture;
c) adding at least one labeled nucleotide or nucleotide analog to the mixture resulting from step b), under conditions suitable for extension of an oligonucleotide, such that when a hybrid of the target restriction fragment and the oligonucleotide is present, and said at least one labeled nucleotide or nucleotide analog is complementary to the at least one unpaired nucleotide of said target restriction fragment directly adjacent to the 3' end of the oligonucleotide sequence, the nucleotide sequence is extended with the labeled nucleotide or nucleotide analog; and
d) detecting the presence or absence of any hybrid(s) with (an) added labeled nucleotide(s) or nucleotide analog (s), or of any oligonucleotide sequence with (an) added labeled nucleotide(s) or nucleotide analog(s).

* * * * *